United States Patent [19]
Moser

[11] Patent Number: 5,123,928
[45] Date of Patent: Jun. 23, 1992

[54] KNEE JOINT ENDOPROSTHESIS

[75] Inventor: Heinz Moser, Oestrich-Winkel, Fed. Rep. of Germany

[73] Assignee: Eska Medical Luebeck Medizintechnik GmbH, Fed. Rep. of Germany

[21] Appl. No.: 548,042

[22] Filed: Jul. 5, 1990

[30] Foreign Application Priority Data

Jul. 7, 1989 [DE] Fed. Rep. of Germany ..... 39222942

[51] Int. Cl.$^5$ ............................................. A61F 2/38
[52] U.S. Cl. ...................................................... 623/20
[58] Field of Search ........................................ 623/20

[56] References Cited

U.S. PATENT DOCUMENTS

| 4,016,606 | 4/1977 | Murray et al. | 623/20 |
| 4,064,568 | 12/1977 | Grundei et al. | 623/20 |
| 4,714,471 | 12/1987 | Grundei | 623/20 |
| 4,950,298 | 8/1990 | Gustilo et al. | 623/20 |

FOREIGN PATENT DOCUMENTS

| 0175989 | 6/1989 | European Pat. Off. |
| 2549819 | 5/1977 | Fed. Rep. of Germany. |
| 2728427 | 1/1979 | Fed. Rep. of Germany. |
| 2744710 | 4/1979 | Fed. Rep. of Germany. |
| 3309896 | 8/1986 | Fed. Rep. of Germany. |

OTHER PUBLICATIONS

"The Noiles Total Knee Prosthesis".
Sheehan, J. M., "Sheehan Knee Prostheses". Zimmer Deloro Surgical Ltd. Mar., 1981.

Primary Examiner—Alan Cannon
Assistant Examiner—Elizabeth M. Burke
Attorney, Agent, or Firm—Panitch Schwarze Jacobs & Nadel

[57] ABSTRACT

A knee joint endoprosthesis is provided, having a femur component to be anchored by a shaft and equipped with two gliding runners, which between them define a hollow space extending anteriorly to posteriorly and open toward the tibia, and a tibia component also to be anchored by a shaft and having two gliding surfaces on which the gliding runners of the femur component can execute rolling and gliding movement. The knee joint endoprosthesis is characterized by the tibia component being equipped with a double truncated cone, which is arranged with its main axis toward the femur and which serves as a guiding and stress reducing element. Further, a pair of guiding surfaces is constructed in the hollow space of the femur component. These surfaces are inclined at angles corresponding respectively to the angles of inclination of the two half truncated cones that form the double truncated cone. The cone surfaces of the half truncated cones are partially surrounded by and glide upon the pair of guiding surfaces.

7 Claims, 6 Drawing Sheets

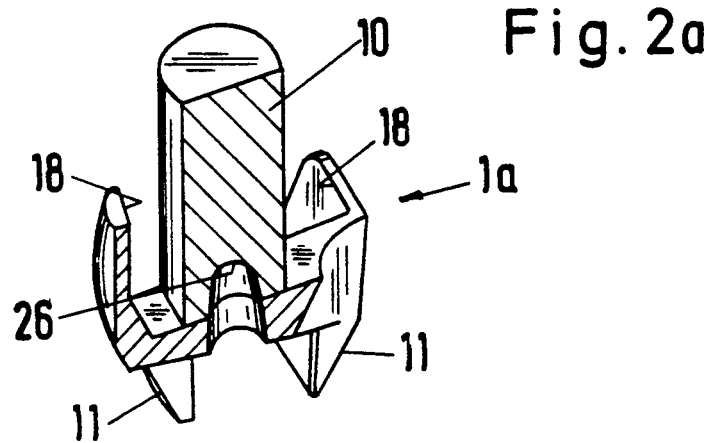
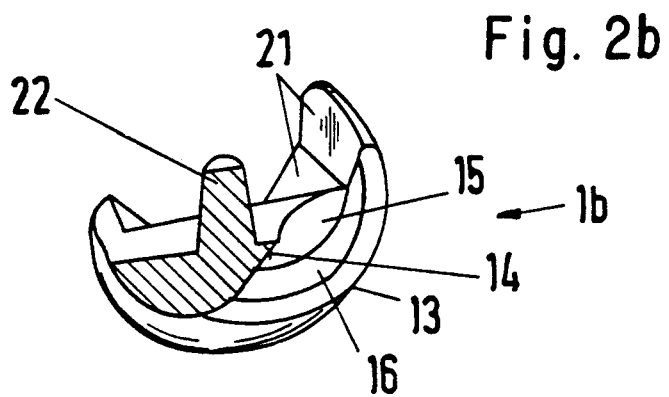
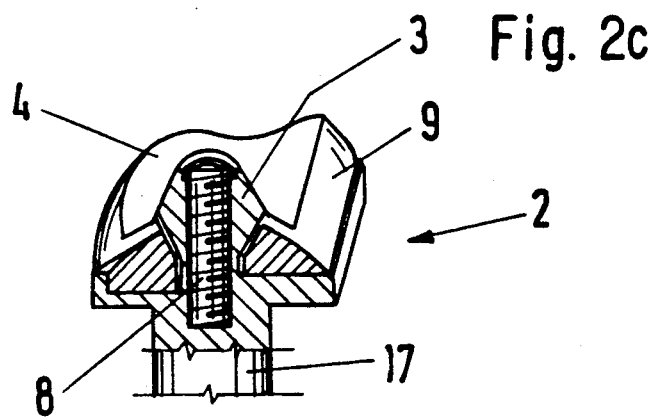

KNEE JOINT ENDOPROSTHESIS

FIELD OF THE INVENTION

The invention concerns a knee joint endoprosthesis for implantation for new parts or replacement of worn parts. More particularly, the invention is directed to a knee joint endoprosthesis with improved reproducibility of joint movement and improved guiding and stress reducing functions.

BACKGROUND OF THE INVENTION

An endoprosthesis of the general type of the invention is known under the designation "Insall/Burstein" Total Knee System from a brochure of the firm Zimmer, USA. A single crosspiece located between the gliding surfaces of the tibia component serves as the guiding or conduction element for the femur component of this known endoprosthesis. When the joint is in the extended position, this crosspiece engages an opening in the hollow space defined between the gliding runners of the femur portion. With increasing flexure of the joint, this crosspiece comes out of engagement with this opening. Conduction of the gliding runners occurs exclusively when the flat lateral surfaces of the aforementioned crosspiece come into contact with the equally flat guiding surface of the femur component.

Disadvantages of this endoprosthesis are its insufficient guiding function, as well as only limited stress reducing capability of the crosspiece during weight shifting movements. High incidence of abrasion or wear on the parts which rest against each other as well as inadequately reproducible physiologic movement of the joint are the results of the structure of the known endoprosthesis.

The purpose of the present invention is to remedy these problems. In addition, an additional aspect of the invention is its use in facilitating the implantation of new parts or, if necessary, the replacement of worn out parts.

SUMMARY OF THE INVENTION

According to the present invention, the tibia component is equipped with a double truncated cone, which is arranged with its main axis toward the femur and which acts as a guiding and stress reducing element. A pair of guiding surfaces is constructed in the hollow space defined between the gliding runners of the femur component. These guiding surfaces are inclined at angles corresponding to the angles of inclination of the respective half truncated cones that form the double truncated cone and partially surround them, and are in gliding relation with the cone surfaces of the half truncated cones.

Depending upon the selection of size of the gap between the double truncated cone and the guiding surfaces in the hollow space, a reduction in stress occurs during weight-shifting movements, not only in the form of a reduction in the stresses acting laterally on the joint, but additionally a partial absorption of the forces acting on the joint along its main axis, thereby easing the stress on the gliding runners and gliding surfaces of the respective femur and tibia components. The latter is particularly the case when there are only very small gaps between the double truncated cone and the pair of guiding surfaces. This causes a reduction in the incidence of wear on the gliding runners and gliding surfaces. In any case, however, the gaps are selected in such a way that the stress of weight-shifting movements is reduced by the double truncated cone.

The physiological course of movement of a healthy knee joint can be especially well reproduced with the present endoprosthesis, if the two gliding surfaces of the tibia component are separated by two struts, which border the double truncated cone and are arranged to extend posteriorly and anteriorly, whereby the posterior strut (that is, in the direction of walking as seen from behind) is wider than the anterior strut. By this means, when the joint is in a bent position, play is permitted between the joint parts, which is the case with a healthy knee. On the other hand, when the joint is in the extended position, just as with a natural knee there is almost no play. Between these two extreme positions the degree of play increases continuously starting from the extended position.

The angles of inclination of both half truncated cones that form the double truncated cone are not always necessarily the same. However, to ensure a symmetrical surface pressure on the double truncated cone it is advantageous if both angles of inclination are equal. In this case, the pair of guiding surfaces in the hollow space of the femur component is also inclined to the same degree, corresponding to the angles of inclination of the half truncated cones.

The double truncated cone can easily be removably connected to the tibia component with a screw inserted axially through it. In case an intolerable degree of wear has occurred after the prosthesis has been in place for a while, this embodiment permits the double truncated cone to be replaced without the need to replace the entire tibia component anchored in the tibia.

The double truncated cone is preferably made out of a durable plastic, such as polyethylene or polyacetal. To strengthen the double truncated cone, it can be coated with metal.

It is advantageous to construct the gliding surfaces of the tibia component in the form of a plastic overlay that is removably connected to the tibia and has a low coefficient of friction, such as polyethylene. In this case, the rest of the tibia component is made of metal. This embodiment permits the replacement of the plastic overlay eventually necessitated by wear after the prosthesis has been in place for a while without the need to replace the entire tibia component.

In addition, it is advantageous to construct the femur component in two parts. In this case, a first part has a shaft, by which it can be anchored in the femur bone. The first part has mating surfaces for a second part with a complementary construction toward the femur and which can be securely connected to the first part by means of a conical clamp. Furthermore, a tight fit is formed between both parts. In this case, the second part contains the gliding runners.

Constructing the femur component in two parts facilitates, on the one hand, the implantation of the endoprosthesis. Only after the first part has been implanted in the femur bone is the second part connected to the first part and brought into engagement with the tibia component. On the other hand, however, constructing the femur component in two parts also makes it possible to replace the part containing the gliding runners without having to remove the part anchored in the femur bone.

In all embodiments the femur component is preferably made of metal, in order for it to withstand the stresses that occur. Furthermore, the femur component can be constructed in such a manner so that it has chock surfaces, on which the parts of the prepared (cut-off) bone come into contact. A solid and definitive installation is hereby made possible. When these surfaces are provided with an open celled, metallic structure, bone fibrils can grow into this structure, which provides the component with a more secure and lasting hold.

All other components of the endoprosthesis that come directly into contact with bone material, especially the shafts of the femur and tibia components, can also be advantageously provided with an open-celled metallic structure, in order to enable bone material to grow into them.

BRIEF DESCRIPTION OF THE DRAWINGS

The foregoing summary, as well as the following detailed description of a presently preferred embodiment of the invention, will be better understood when read in conjunction with the appended drawings. It is understood, however, that this invention is not limited to the precise arrangements illustrated:

FIG. 2 are perspective cross-section views of (a) the shaft portion of the femur component, (b) the gliding surfaces of the femur component, and (c) the tibia component;

DETAILED DESCRIPTION OF PREFERRED EMBODIMENT

Figure 1A:
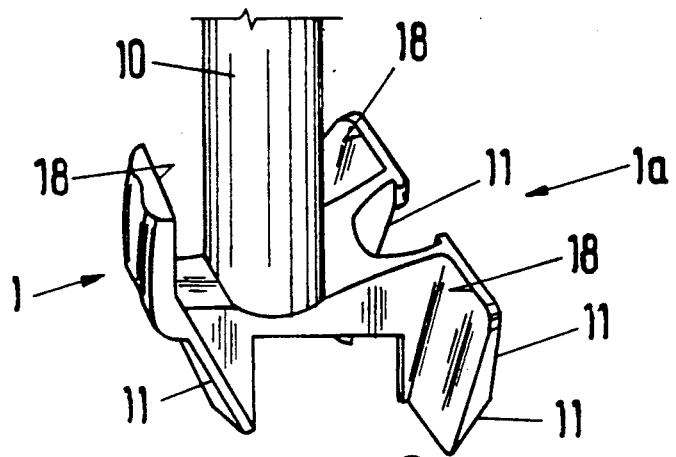
FIG. 1 are perspective views (a) the shaft portion of the femur component, (b) the gliding surfaces of the femur component, and (c) the tibia component of the knee joint endoprosthesis in an embodiment with a two-part femur component.

In the following description, like components are designated with the same reference numbers. In the drawings, only an embodiment of the knee joint endoprosthesis is shown whereby the femur component is constructed in two parts. However, the invention is not limited to this embodiment.

Figure 1B:
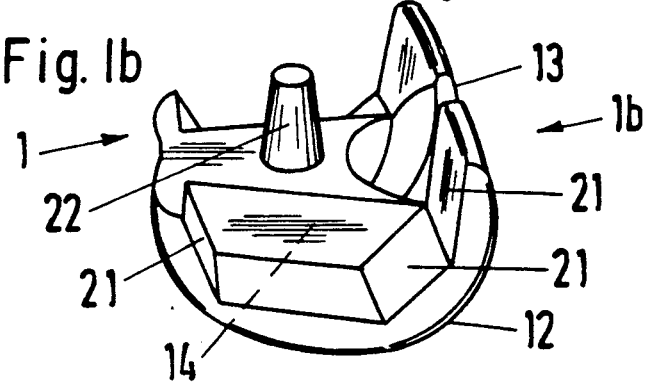
Figure 1C:
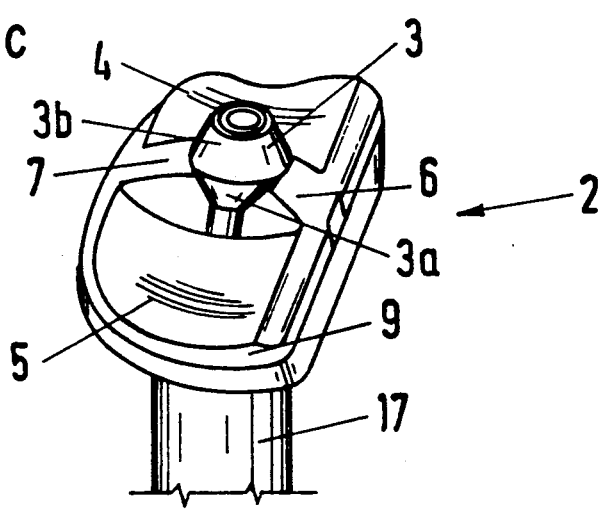

In FIG. 1 perspective views of the knee joint endoprosthesis are shown, consisting of, in this case, the two-part femur component 1 with the parts 1a and 1b, as well as the tibia component 2.

Part 1a has a shaft 10, which can be anchored in the femur bone. It is equipped with chock surfaces 18, on which parts of the femur bone prepared for the implantation come into contact. Toward the tibia part 1a has mating surfaces 11, which lie snugly within the corresponding mating surfaces 21 after part 1a is fitted together with part 1b.

By means of a conical clamp 22 located on part 1b and a corresponding clamp housing 26 (see FIG. 2), both parts 1a and 1b can be securely connected in order to build the femur component 1.

Part 1b carries the gliding runners 12, 13. Between the two gliding runners 12, 13, a hollow crosspiece extends toward the tibia, by which a hollow space 14 is defined. As will be discussed below, a pair of guiding surfaces are constructed in this hollow space 14.

The tibia component 2 also has a shaft 17 that can be anchored in the bone. Component 2 has two gliding surfaces 4, 5, upon which the gliding runners 12, 13 of the femur component can roll or glide. In the embodiment shown, the gliding surfaces 4, 5 are constructed of a plastic overlay 9.

The double truncated cone 3 with which the tibia component 2 is provided serves as a guiding and stress-reducing element. It consists of two half truncated cones 3a, 3b joined together at their bases.

The two gliding surfaces 4, 5 are separated by struts 6, 7 extending posteriorly and anteriorly and partially enclosing the double truncated cone, whereby the posterior strut 6 is wider than the anterior strut 7. By this means, there is play in the joint when in the bent position, whereas there is practically no play when the joint is in the extended position.

In FIG. 2, perspective cross-sectional views of the components of the endoprosthesis of FIG. 1 are shown. In the cross-sectional view of part 1a, the conical clamp housing 26 is clearly discernible, in which the conical clamp 22 of part 1b can be inserted to create a conical clamp connection.

The cross-sectional view of part 1b shows the guiding surfaces 15, 16 located in the hollow space 14, which are respectively inclined into this space. They are inclined specifically at angles that correspond respectively to the angles of inclination of the two half truncated cones 3a, 3b, so that the cone surfaces of the half truncated cone 3a can come into gliding contact with guiding surface 16 and those of the half truncated cone 3b can glide on guiding surface 15.

In the embodiment shown, the double truncated cone 3 is removably connected to the tibia component 2 by means of a screw 8 inserted axially through it. The screw also thereby secures the seating of the plastic overlay 9 onto the tibia component 2, which can be otherwise made of metal.

Figure 3B:
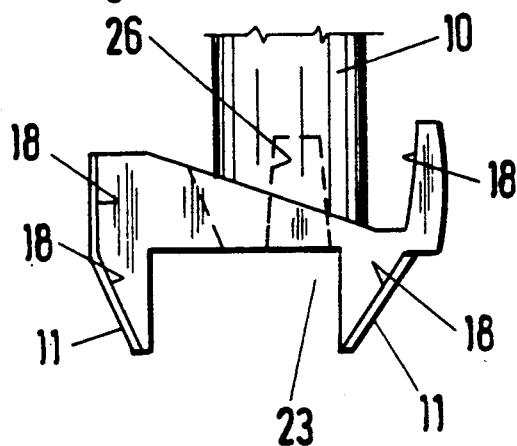
FIG. 3 is a perspective view (a) of the component of the endoprosthesis to be anchored in the femur bone, its side view (b), and top view (c)
Figure 3A:
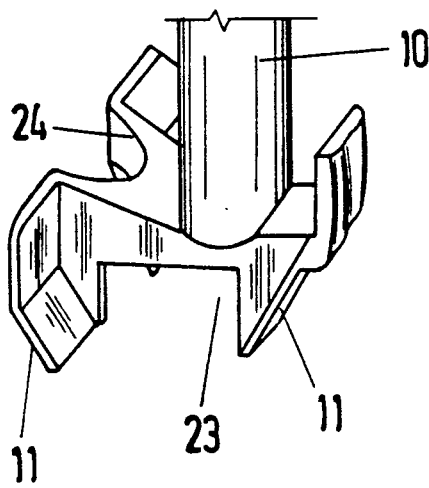
Figure 3C:
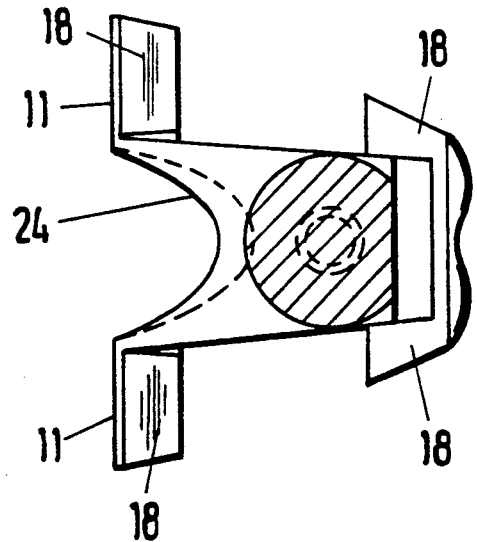

Additional details of part 1a are evident in FIG. 3. The indentation 23, which is bounded by the flanges containing the chock surfaces 18 as well as the mating surfaces 11, is constructed in such a manner so that it can fit perfectly over the crosspiece that defines the hollow space 14 in part 1a when the prosthesis is assembled.

On its posterior side, part 1a has a recess 24 designed in a way so that it can be conveyed over the double truncated cone 3, and specifically only during implantation when the joint is completely bent.

Figure 4A:
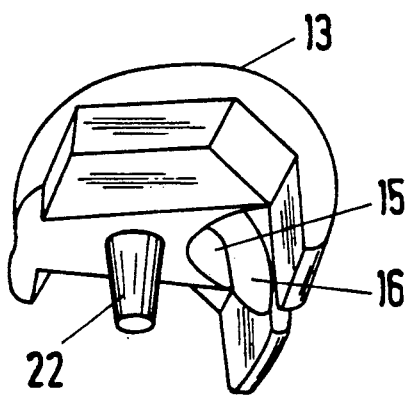
FIG. 4 is a perspective view (a) of the part of the femur component of the endoprosthesis containing the gliding runners, its cross-sectional side view (b), and top view (c)
Figure 4B:
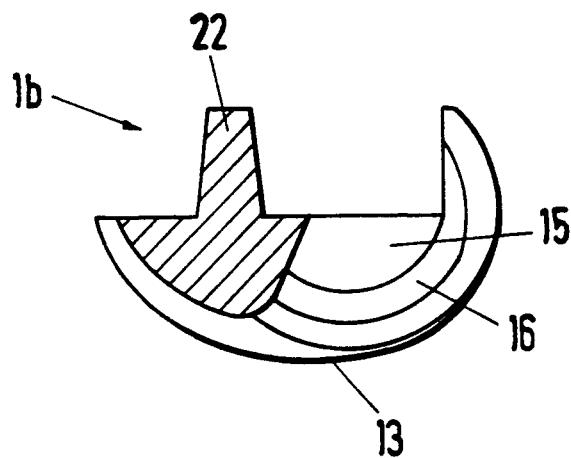
Figure 4C:
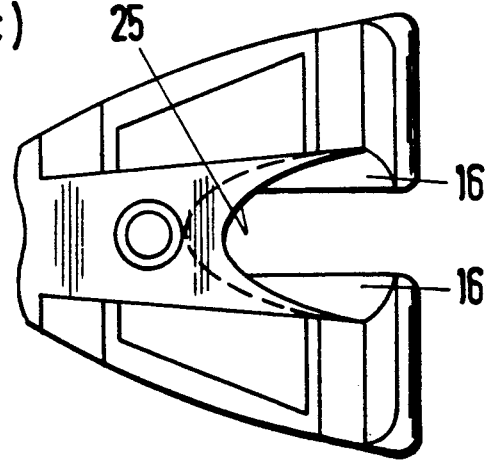

Additional details of part 1b are evident in FIG. 4. As discussed above, the pair of guiding surfaces 15, 16 is located in the hollow space 14. These surfaces are inclined in the interior of the hollow space at angles corresponding respectively to the angles of inclination of the half truncated cones 3a, 3b. A posterior recess 25 is proportioned corresponding to the recess 24 in part 1a and primarily permits the femur component 1 to be conveyed over the double truncated cone 3. The gliding runners 12, 13 of part 1b are constructed in a known curved shape.

Figure 5A:
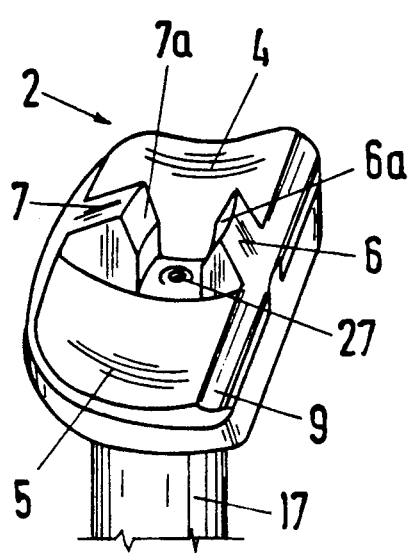
FIG. 5 is a perspective view (a) of the tibia component without the double truncated cone, its side view (b), and top view (c)
Figure 5B:
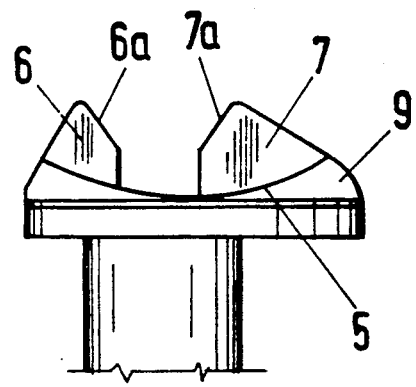
Figure 5C:
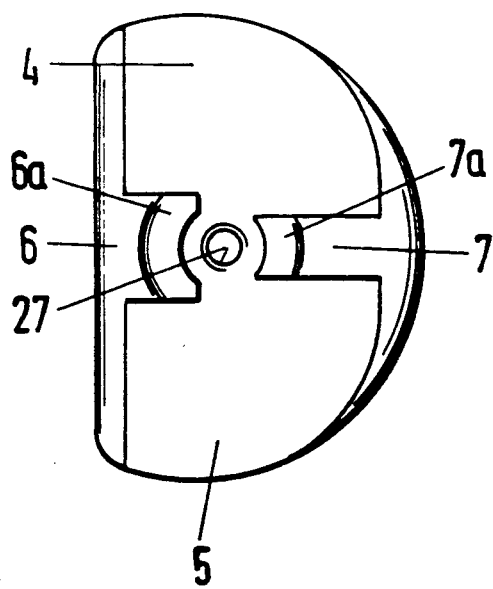

Additional details of the tibia component 2 are illustrated in FIG. 5. For the sake of clarity, the double truncated cone has been omitted.

The borehole 27 is clearly visible, into which a screw 8 can be screwed to removably attach the double truncated cone and to fix the plastic overlay 9 onto the tibia component 2. The gliding surfaces 4, 5 are formed in the plastic overlay 9 in a known curved shape.

The struts 6, 7 separating the gliding surfaces 4, 5 are sloped on their facing surfaces 6a, 7a, and specifically at an angle which corresponds to the angle of inclination of the half truncated cone 3a. By this means, the double truncated cone is enclosed.

Figure 6:
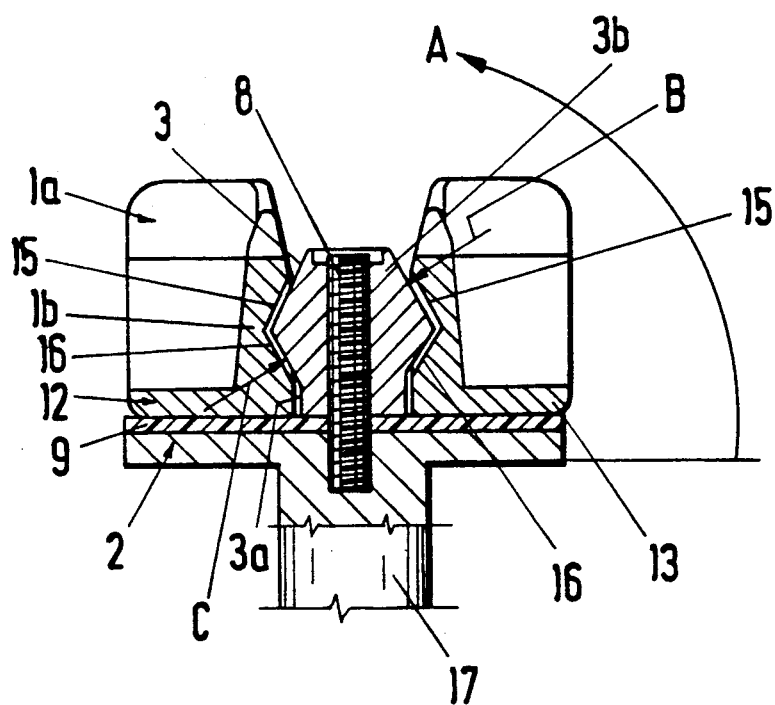
FIG. 6 is a cross-sectional front view of the assembled endoprosthesis in the area of the double truncated cone.

FIG. 6 shows the assembled endoprosthesis in cross section. It is clearly evident that the double truncated cone 3 is tightly constrained by the pair of guiding surfaces 15, 16. Accordingly, a breaking loose from the femur parts 1a, 1b under stress is not possible. At the same time, however, the ability of the joint to turn is guaranteed.

The advantage of constructing the guiding and stress reducing element as a double truncated cone 3 becomes especially clear when the joint is undergoing a weight-shifting movement, as indicated by arrow A. In this instance, the forces occurring as a result of this movement are transferred to the double truncated cone 3 over the one guiding surface of the pair of guiding surfaces 15 and the cone surface of the upper half truncated cone 3b in the direction of arrow B, as well as over the one guiding surface of the pair of guiding surfaces 16 and the cone surface of the lower half truncated cone 3a in the direction of arrow C. It is clear that the forces in the direction of arrow B and arrow C are relatively equal; however, they work against each other. The forces accordingly cancel each other out, so that the remaining components of the joint are not subject to stress, not even the screw 8.

In the embodiment shown, the angles of inclination of both half truncated cones are approximately equal. In this way, an even surface pressure is produced on the surfaces of the half truncated cones 3a, 3b when a weight-shifting movement takes place.

If the gaps between the pair of guiding surfaces 15 and the upper half truncated cone 3b are small enough, for example, then an additional partial absorption of the forces acting on the joint along its main axis can also take place, thereby easing the stress on the gliding runners 12, 13 and the gliding surfaces 4, 5.

The present invention may be embodied in other specific forms without departing from the spirit or essential attributes thereof and, accordingly, reference should be made to the appended claims, rather than to the foregoing specification as indicating the scope of the invention.

I claim:

1. A knee joint endoprosthesis comprising a femur component (1) to be anchored by means of a shaft (10), having two gliding runners (12, 13), which between them define a hollow space (14) extending anteriorly to posteriorly and open toward the tibia, and a tibia component (2) to be anchored by means of a shaft (17), having two gliding surfaces (4, 5) upon which the gliding runners (12, 13) of the femur component (1) can execute rolling and gliding movements, characterized by the tibia portion (2) being equipped with a double truncated cone element (3), which is arranged with its main axis toward the femur and which acts as a guiding and stress reducing element, and a pair of guiding surfaces (15, 16) arranged within the hollow space (14) of the femur component (1), which are inclined at angles corresponding respectively to the angles of inclination of the two half truncated cones (3a, 3b) that form the double truncated cone (3), which partially surround them, and upon which the cone surfaces of the half truncated cones glide.

2. A knee joint endoprosthesis according to claim 1 wherein the gliding surfaces (4, 5) of the tibia component (2) are separated by two struts (6, 7), which partially enclose the double truncated cone and which are arranged to extend posteriorly and anteriorly, whereby the posterior strut (6) is wider than the anterior strut (7).

3. A knee joint endoprosthesis according to claim 1 wherein the angles of inclination of the two half truncated cones (3a, 3b) are substantially the same.

4. A knee joint endoprosthesis according to claim 1 wherein the double truncated cone (3) is removably connected to the tibia component (2) with a screw (8) inserted axially through it.

5. A knee joint endoprosthesis according to claim 1 wherein the double truncated cone (3) comprises a durable plastic.

6. A knee joint endoprosthesis according to claim 1 wherein the gliding surfaces (4, 5) of the tibia component (2) comprise a plastic overlay that is removably connected to the tibia component and have a low coefficient of friction.

7. A knee joint endoprosthesis according to claim 1 wherein the femur component (1) comprises two parts (1a, 1b), wherein the first part (1a) can be anchored with a shaft (10) and has mating surfaces (11) for the second part (1b), which can be connected to the first part (1a) by means of a conical clamp (22) and which also carries the gliding runners (12, 13).

* * * * *